United States Patent [19]

Cobb

[11] Patent Number: 4,551,573
[45] Date of Patent: Nov. 5, 1985

[54] ALKYLATION OF AROMATIC COMPOUNDS

[75] Inventor: Raymond L. Cobb, Bartlesville, Okla.

[73] Assignee: Phillips Petroleum Company, Bartlesville, Okla.

[21] Appl. No.: 655,825

[22] Filed: Oct. 1, 1984

[51] Int. Cl.$^4$ ............................ C07C 2/64; C07C 2/68
[52] U.S. Cl. ..................................... 585/459; 585/446
[58] Field of Search ......................................... 585/459

[56] References Cited

U.S. PATENT DOCUMENTS

| | | | |
|---|---|---|---|
| 2,803,682 | 8/1957 | McCaulay et al. | 267/671 |
| 3,284,523 | 11/1966 | Beck et al. | 260/668 |
| 3,306,943 | 2/1967 | Sulo et al. | 585/459 |
| 3,379,787 | 4/1968 | Amir | 260/671 |
| 3,395,191 | 7/1968 | Cier | 260/671 |
| 3,686,339 | 8/1972 | Schecker et al. | 260/668 F |
| 3,848,012 | 11/1974 | Applegath et al. | 585/459 |
| 3,849,507 | 11/1974 | Zuech | 260/671 C |
| 3,856,875 | 12/1974 | Wood | 260/668 F |
| 4,284,818 | 8/1981 | Sato et al. | 260/586 |
| 4,319,067 | 3/1982 | Kreeger | 585/459 |

FOREIGN PATENT DOCUMENTS 1441718  7/1976  United Kingdom.

OTHER PUBLICATIONS

Drahowzal, F. A. in Olah, Friedel-Crafts & Related Reactions, Interscience, 1964, vol. VII, pp. 417–418.

*Primary Examiner*—D. E. Gantz
*Assistant Examiner*—Helane Myers
*Attorney, Agent, or Firm*—S. E. Reiter

[57] ABSTRACT

The alkylation of aromatic compounds with olefinic compounds is catalyzed by catalyst consisting essentially of aluminum halide and elemental iodine.

25 Claims, No Drawings

ALKYLATION OF AROMATIC COMPOUNDS

BACKGROUND

This invention relates to alkylation processes. In another aspect, the invention relates to alkylation of aromatic compounds with olefinic compounds. In a further aspect, the invention relates to the production of alkyl aromatic compounds. In yet another aspect, the invention relates to the production of cyclialkylated aromatic compounds.

Friedel-Crafts, i.e., acid catalyzed alkylation of aromatics, is a well-known reaction. When aromatics are alkylated with an alkyl halide, substantial quantities of hydrogen halide are produced as a by-product of the reaction. Not only are the starting alkyl halides frequently costly and the formation of hydrogen halide as a by-product wasteful, in addition, the by-product hydrogen halide may create a handling and disposal problem due to its corrosive nature. In order to alleviate the above-mentioned problems, aromatics can be alkylated with olefinically unsaturated compounds frequently instead of with alkyl halides. However, prior art reactions of aromatic compounds with olefinically unsaturated compounds frequently suffer from low conversion of reactants, poor selectivity to the desired alkylated product(s), i.e. many by-products may be formed, and slow reaction rates, i.e. sluggish reaction occurs.

OBJECTS OF THE INVENTION

An object of the invention, therefore, is a process to alkylate aromatic compounds with olefinic compounds to give alkylated aromatic compounds in high yield, i.e. high levels of reactant conversion and high selectivity to the desired alkylated product(s).

Another object of the invention is an alkylation process with substantially improved reaction rate compared to prior art processes.

These and other objects of my invention will become more apparent from the disclosure and claims herein provided.

STATEMENT OF THE INVENTION

In accordance with the present invention, I have discovered that the reaction rate, feed conversion and product selectivity of the aluminum halide promoted alkylation of aromatic compounds with olefinically unsaturated compounds are all surprisingly improved by the addition of elemental iodine to the reaction mixture.

DETAILED DESCRIPTION

Thus, in accordance with the present invention, a process is provided comprising contacting at least one aromatic compound with at least one olefinic compound in the presence of a catalyst consisting essentially of aluminum halide and elemental iodine.

In accordance with another embodiment of the invention, alkylated aromatic product is prepared by adding at least one reactant aromatic compound and at least one olefinic compound to a slurry prepared by combining an aluminum halide and elemental iodine in an aromatic medium, wherein the aromatic medium is selected from the reactant aromatic compound and the alkylated aromatic product or mixtures thereof.

REACTANTS

The process of the present invention comprises contacting at least one aromatic compound with at least one olefinic compound. Suitable aromatic compounds are broadly contemplated to include those compounds which are capable of undergoing Friedel-Crafts alkylation reaction. Thus, monocyclic as well as polycyclic aromatic compounds are suitable for the practice of the invention. Preferably, the aromatic compounds employed in the practice of the invention will be monocyclic, bicyclic or tricyclic aromatic compounds having 6 up to about 30 carbon atoms. Thus, benzene, naphthalene, anthracene, phenanthrene, and derivatives thereof are contemplated to be within the scope of the present invention.

An especially preferred group of aromatic compounds useful in the practice of my invention conform to the general formula

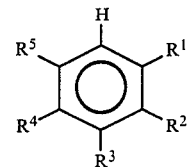

wherein each $R^1$, $R^2$, $R^3$, $R^4$, and $R^5$ is independently selected from hydrogen, and $C_1$ through $C_{10}$ alkyl or cycloalkyl radicals. When aromatic compounds which conform to the above formula are used for alkylation reactions, a variety of useful chemical intermediate and chemical products can be obtained.

Examples of aromatic compounds which satisfy the above formula include benzene, toluene, meta-xylene, tertiary-butylbenzene, and the like.

When it is desired that the aromatic compound yield a cyclialkylated aromatic product upon alkylation, then it is preferred that $R^1$ in the above formula be a methyl, or ethyl and that $R^4$ be a secondary alkyl group having 3 to about 10 carbon atoms and only one alpha-hydrogen. Examples of aromatic compounds useful for the cyclialkylation reaction include para-cymene (para-isopropyltoluene), para-methylcyclohexylbenzene, para-methylcyclopentylbenzene, para-ethylcyclopentylbenzene, para-ethylcyclohexylbenzene and the like.

Suitable olefinic compounds are broadly contemplated to be organic compounds having at least one carbon-carbon double bond and any substituents which do not detrimentally interact with the catalyst employed for the alkylation reaction. Preferred olefinic compounds employed in the practice of the invention are mono-olefins. Those mono-olefins having 4 up to about 30 carbon atoms with only one carbon-carbon double bond, and are capable of forming tertiary carbocations under the alkylation process conditions are especially preferred, because the possibility of multiple alkylation reactions with consequent formation of a mixture of products is minimized.

The especially preferred group of olefinic compounds useful in the practice of my invention can also be described by the formula

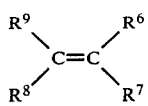

wherein each of $R^6$, $R^7$, $R^8$ and $R^9$ are independently selected from hydrogen and $C_1$ through $C_{10}$ alkyl or cycloalkyl radicals. In addition, $R^6$ and $R^7$ can be joined as part of a polymethylene radical or a halogen-, alkyl- or cycloalkyl-substituted polymethylene radical having about 2 to about 20 carbon atoms, i.e., a carbocyclic compound with an exocyclic double bond. Further, $R^6$ and $R^9$ can be similarly joined as part of a polymethylene radical or a halogen-, alkyl-, or cycloalkyl-substituted polymethylene radical having about 2 to about 20 carbon atoms, i.e., a carbocyclic compound with an endocyclic double bond.

Examples of olefinic compounds useful in the practice of the invention include isobutylene, 2-methyl-1-butene, 2-methyl-2-butene, 2,3-dimethyl-2-butene, neohexene(tertiary-butylethylene), diisobutylene(2,4,4-trimethyl-1-pentene), 2-butene, 2-pentene, 1-methylcyclohexene, 1-methylcyclopentene, 2-hexene, and the like.

In accordance with a specific embodiment of the invention, a mixture of olefinic compounds can be employed in the cyclialkylation reaction. Since one molecule of olefin is reduced to a saturated aliphatic compound for each molecule of olefin which reacts with the reactant aromatic compound, the mixture of olefins employed can be chosen so that the first olefin will be more readily protonated, i.e., a better hydrogen acceptor, under the Friedel-Crafts alkylation reaction conditions of the invention compared to the second olefin. Thus, the first olefin, which is a better hydrogen acceptor, will be preferentially reduced to a saturated aliphatic compound to be recovered as a reaction by-product and will not become part of the cyclialkylated aromatic product. The first olefin can therefore be seen as a sacrificial agent, i.e., participating in the reduction step which does not produce cyclialkylated product, while the second olefin or cyclialkylating olefin, is more efficiently utilized for the production of cyclialkylated aromatic product.

As an example of the use of a mixture of two olefinic compounds, isobutylene and neohexene can be advantageously employed together for the cyclialkylation of an aromatic substrate. Although isobutylene is a useful cyclialkylating olefin when employed in the absence of other olefins, isobutylene functions as a sacrificial agent when used in admixture with an olefin which is not as readily protonated in the presence of a catalyst consisting essentially of $AlCl_3$-$I_2$, such as neohexene. Thus, while a substantial proportion of the neohexene is incorporated into the cyclialkylated aromatic product, a substantial proportion of the isobutylene is reduced to isobutane under the reaction conditions. The use of a mixture of olefins, as illustrated by this example, is particularly useful where a more readily available, less expensive olefin such as isobutylene also functions as a better hydrogen acceptor than a less readily available, more expensive olefin such as neohexene. Thus, the more valuable olefin, neohexene, is preferentially incorporated into the cyclialkylated aromatic product, while the less costly olefin, isobutylene, is preferentially consumed in the non-productive reduction step.

PRODUCTS

The products of the alkylation reaction of the invention are of two general types, i.e. alkylated aromatic products and cyclialkylated aromatic products. Alkylated products can be a wide variety of aromatic compounds represented by the formula

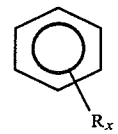

wherein each R is independently a $C_1$ through $C_{40}$ alkyl or cycloalkyl radical and x is an integer from at least one up to 6. One or more of the R groups may be halogen, but not all R groups of the product are halogen.

Two common cyclialkylated products are the indanes and tetralins. Indanes have the following structure:

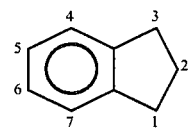

Depending on the substitution pattern of the starting aromatic and olefinic compounds employed, a wide variety of substitution patterns can be achieved in the indane products prepared in accordance with the invention.

Tetralins, or tetrahydronaphthalenes, have the following structure:

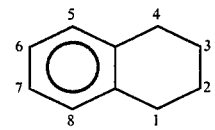

As with the indane products, a wide variety of substitution patterns can be achieved in the tetralin products prepared in accordance with the invention.

The alkylated products of the invention find a wide range of uses, such as for example as reaction solvents, as chemical intermediates for the production of fragrance chemicals, as chemical intermediates for the production of herbicides and so on.

CATALYST

The catalyst employed in the process of the present invention consists essentially of aluminum halide and elemental iodine, although it should be recognized that additional catalyst components which do not detrimentally affect the performance of the alkylation catalyst can also be present. The aluminum halide component can be represented as $AlX_3$ wherein each X is independently selected from the halogens. Thus, suitable aluminum halide compounds include aluminum tribromide ($AlBr_3$), dichloroaluminum bromide ($AlCl_2Br$), dibromoaluminum fluoride (AlBr$_2$F), aluminum triiodide (AlI$_3$), aluminum chloride (AlCl$_3$) and the like and mixtures of any two or more thereof. Aluminum chloride is the presently preferred aluminum halide because it is readily available and provides a selective as well as a reactive catalyst.

The catalyst components, i.e. AlX$_3$ and I$_2$, can be combined in any suitable ratio as can be readily determined by one skilled in the art. For purposes of guidance, it is suggested that a weight ratio of I$_2$:AlX$_3$ of about 0.01:1 up to about 1:1 be employed. It is preferred, for most efficient use of reagents and for optimum catalyst performance, that a weight ratio of I$_2$:AlX$_3$ of about 0.1:1 to about 0.4:1 be employed.

The catalyst components can be combined in any suitable manner as readily determined by those skilled in the art. Thus, catalyst components can be dry mixed, slurried in a solvent which is not reactive under the reaction conditions employed, slurried in the reactant aromatic compound, slurried in an aliquot of the alkylated aromatic product or combined by other suitable techniques.

Although the catalyst can withstand the presence of small amounts of moisture, it is preferred that care be taken to exclude the presence of moisture from the reaction medium. While optional, it is preferred that catalyst preparation as well as the alkylation reaction be carried out in an inert atmosphere, i.e., in the presence of a gas such as N$_2$, Ar and the like.

REACTION CONDITIONS

The molar ratio of olefinic compound to aromatic compound employed in the practice of the invention can vary broadly. In order to provide further guidance, it is suggested that a molar ratio of olefinic compound to aromatic compound of at least about 0.05:1 up to about 5:1 be employed. Ratios below the lower value provide low product yield based on the amount of starting material employed, while ratios above the upper value have a tendency to produce undesirable levels of by-products due to multiple alkylation reactions of the aromatic ring, olefin rearrangement and the like. Ratios of about 0.2:1 up to about 3:1 are preferred for efficient use of starting materials and minimum formation of by-products, which in turn simplifies the task of product recovery.

While any ratio of first olefin to second olefin can be utilized when mixtures of olefinic compounds are employed, it is preferred that the second olefin, i.e., the cyclialkylating olefin, be present in about 20 to 40 mole % excess relative to the first olefin, i.e., the sacrificial olefin. When the amounts of reagents employed are maintained within the preferred range, most efficient incorporation of the second olefin, i.e., the cyclialkylating olefin, into cyclialkylated aromatic product occurs. At the same time, the first olefin, i.e., the sacrificial olefin, is preferentially reduced to a saturated compound, rather than forming additional cyclialkylated aromatic product.

The alkylation reaction of the invention can be carried out in any suitable vessel which provides efficient contacting between the catalyst components and the reactants. For simplicity, a stirred batch reactor can be employed. The material of construction of the reaction vessel should be chosen so as to be resistant to the possibly corrosive nature of the catalyst. Thus, a glass-lined vessel, Hastelloy C or other resistant alloys as are known in the art are suitable. The major requirement which any reaction vessel must satisfy is the ability to provide rapid, efficient mixing since the alkylation reaction of the invention catalyzed by AlX$_3$-I$_2$ is frequently a very rapid reaction.

The molar ratio of AlX$_3$ to reactant aromatic compound can be readily determined by those skilled in the art. In order to provide guidance, it is suggested that a molar ratio of at least about 0.001 moles of AlX$_3$ per mole of reactant aromatic compound up to a molar ratio of about 1:1 be employed. Preferably, a molar ratio of about 0.01:1 to about 0.5:1 will be employed for most efficient utilization of reagents.

Because the alkylation reaction carried out according to the invention is generally quite rapid, temperature requirements for the alkylation reaction are quite modest. Broadly, a temperature range of about 0° up to about 130° C. is suitable. Where cyclialkylation is specifically desired, a temperature range of about 20° to about 80° C. is appropriate. The preferred temperature range for cyclialkylation is about 30° to about 65° C., while the preferred temperature range for simple aromatic ring alkylation is about 40° to about 100° C.

It is convenient as a means of temperature control to employ excess reactant aromatic compound or alkylated aromatic product or other diluents which are relatively inert to the reaction conditions employed. When the desired alkylation reaction is rapid and consequently required contact between catalyst and diluent is short, the stability of the diluent under the reaction conditions employed is not as critical as when longer reaction times are employed. In order to minimize by-product formation, however, it is preferred that diluents which do not undergo substantial isomerization, rearrangement, degradation or the like under the reaction conditions be employed. It is especially preferred to use alkylated aromatic product as the diluent for ease of product recovery.

The pressure at which reaction is carried out is not critical. If reaction is carried out in a sealed vessel, autogenous pressure is suitable, although higher or lower pressures can be employed. Reaction can also be carried out at atmospheric pressure in an open reaction vessel, in which case the vessel will preferably be equipped with a moisture trap to prevent significant exposure of catalyst to moisture.

Reaction time is generally quite short and is often dictated by the type of equipment employed. Sufficient time must be provided for thorough contacting of the aromatic compound, the olefinic compound and the catalyst. Although in theory there is no upper limit as to the reaction time which may be employed, reaction is generally quenched shortly after all reagents are contacted to prevent a significant degree of side reactions from occurring. Thus, depending on the type of reaction vessel employed and its stirring capabilities, etc., reaction time could be a matter of seconds to a matter of minutes. Reaction is then quenched and worked up as described in more detail below to prevent a significant degree of product isomerization or degradation from occurring in the continued presence of active catalyst.

PRODUCT RECOVERY

To quench the alkylation reaction, the reaction mixture is poured into water, preferably ice water. After phase separation, the organic layer can be washed additional times with water if desired to aid removal of aluminum halide catalyst. One or more such additional washings can be carried out with dilute alkali solution to further aid aluminum halide removal. Additional washing of the organic layer, as desired, can be carried out with dilute sodium thiosulfate solution to aid removal of residual $I_2$ from the aqueous phase. Pure product is then typically recovered by reduced pressure fractional distillation of the washed reaction mixture.

EXAMPLES

All of the experiments described below were carried out in conventional laboratory glassware equipped with a mechanical stirrer and a nitrogen bubbler to prevent introduction of moisture into the reaction vessel.

Analyses were done by gas liquid chromatography (glc) employing either a 10 foot by ⅛ inch column packed with 5 wt. % SP 1200 and 1.75 wt % Bentone 34 on Supelcoport, a low polarity ester; supplied by Supelco, Inc., Supelco Park, Bellefonte, PA 16823, or a 50 meter capillary column coated with OV 101 silicone fluid; supplied by Ohio Valley Specialty Chemicals, Inc., 115 Industry Rd., Marietta, OH 45750. Analyses on the former column were carried out using a temperature program of 10° C./minute from a starting temperature of 150° C. up to 200° C. Analyses on the latter column were carried out from 50° C. to 250° C. using a temperature program of 10° C./min.

EXAMPLE I

To 90 grams (g) of p-cymene (0.67 mole) were added 7 g of aluminum chloride (0.05 mole) and 2 g of iodine (0.008 mole) under nitrogen atmosphere. The mixture was stirred rapidly and 85 g of neohexene (1.0 mole) was added over a period of about 9 minutes while the temperature was maintained at about 35° C. with external cooling. When neohexene addition was complete, a sample was taken for analysis by glc. The reaction mixture was then stirred an additional 51 minutes at ambient temperature. Samples were also taken at 10 minutes and 51 minutes after completion of the neohexene addition. The analyses of these three samples, as well as analogous samples taken from a control reaction carried out in the absence of iodine are summarized in Table I.

TABLE I

Preparation of Hexamethyltetralin (HMT) from p-Cymene and Neohexene

| Catalyst | Reaction Time, minutes | % Conversion of p-cymene | % Selectivity to HMT |
|---|---|---|---|
| AlCl$_3$—I$_2$ (Invention) | 9 (neohexene addition complete) | 72 | 87 |
| | 19 | 73 | 86 |
| | 60 | 74 | 85 |
| AlCl$_3$ (control) | 8 (neohexene addition complete) | 30 | 82 |
| | 18 | 42 | 81 |
| | 60 | 57 | 82 |
| | 94 | 60 | 82 |

These data demonstrate that the aluminum chloride promoted reaction of neohexene with p-cymene is much more rapid in the presence of iodine than in the absence of iodine. Reaction is essentially complete as soon as the addition of neohexene is complete. By contrast, the control conversion process carried out in the absence of iodine continues for more than an hour after the addition of neohexene is complete.

EXAMPLE II

Changing the ratio of the reactants also affects the rate and course of the reaction. In this example samples were taken periodically during the addition of neohexene to the p-cymeme-catalyst mixture described in Example I, maintained at about 30°–35° C., and analyzed by glc. The effect of varying reactant ratios as the reaction progressed is summarized in Table II for invention catalyst (AlCl$_3$-I$_2$) and control catalyst (AlCl$_3$).

TABLE II

Effect of Reactant Ratios in the Preparation of Hexamethyltetralin (HMT) from p-Cymene and Neohexene

| Catalyst | Mole Ratio, neohexene/ p-cymene | % Conversion of p-cymene | % Selectivity* | | |
|---|---|---|---|---|---|
| | | | HMT | TMIPI | TMMPI |
| AlCl$_3$—I$_2$ (Invention) | 0.40 | 26.7 | 85.0 | 5.9 | 0.3 |
| | 0.80 | 44.1 | 88.8 | 7.9 | 0.8 |
| | 1.20 | 61.3 | 88.0 | 8.4 | 1.3 |
| | 1.60 | 82.4 | 86.6 | 8.8 | 2.1 |
| | 1.84 | 90.7 | 85.6 | 9.0 | 2.5 |
| | 2.07 | 96.8 | 84.1 | 8.8 | 3.2 |
| | 2.31 | 98.7 | 82.6 | 8.6 | 3.5 |
| | 2.55 | 99.0 | 81.8 | 8.5 | 3.9 |
| AlCl$_3$ (Control) | 0.44 | 20.0 | 93.1 | 4.0 | 1.3 |
| | 0.88 | 38.2 | 91.7 | 3.8 | 2.2 |
| | 1.32 | 53.4 | 90.3 | 3.9 | 2.9 |
| | 1.76 | 63.1 | 88.6 | 4.5 | 3.2 |
| | 2.19 | 69.9 | 86.4 | 5.5 | 3.3 |

*HMT = 1,1,3,4,4,6-Hexamethyltetralin.
TMIPI = 1,1,3,5,-Tetramethyl-3-isopropylindane
TMMPI = 1,1,3,5-Tetramethyl-3-(4-methylphenyl)indane from cyclodehydrodimerization of p-cymene.

It is seen by comparing the % conversion of p-cymene and % selectivity to HMT in the invention run that the preferred mole ratio of p-cymene to neohexene is in the range of approximately 1.8 to 2.2, while the % conversion in the control reaction does not similarly reach a level that can be selected as optimum.

EXAMPLE III

The following example demonstrates the use of AlCl$_3$-I$_2$ catalyst in the reaction of p-cymene with isobutylene to produce 1,1,3,3,5-pentamethylindane (PMI). The reaction was conducted as described in Example I except that the isobutylene was introduced into the reaction mixture via a gas dispersion tube over a 30 minute period. A sample was taken immediately upon completion of the isobutylene addition and analyzed by glc. A comparative run with only AlCl$_3$ as the catalyst was then carried out and similarly analyzed after 30 minutes. Table III shows the results of these runs.

TABLE III

Preparation of Pentamethylindane (PMI) from p-Cymene and Isobutylene

| Catalyst | Reactant Mole Ratio | % Conversion of p-Cymene | % Selectivity to PMI |
|---|---|---|---|
| AlCl$_3$—I$_2$ (Invention) | 1.3 | 52 | 99 |
| AlCl$_3$ (Control) | 1.3 | 35 | 95 |

It is seen that the selectivity to PMI is improved with invention catalyst compared to control catalyst. In addition, the rate of p-cymene conversion is much more rapid with invention catalyst, i.e. AlCl$_3$ plus iodine, compared to control catalyst, i.e. AlCl$_3$ alone.

EXAMPLE IV

Another example of the cyclialkylation process of the invention is the production of 1,1,2,3,3,5-hexamethylindane (HMI) from 2-methylbutene-2 and p-cymene. The reaction was conducted as in Example I except that 1.0 mole of p-cymene and 1.4 moles of 2-methylbutene-2 were used. The methylbutene was added over 20–22 minutes and the stirring continued for an additional 60 minutes. Results with invention ($AlCl_3$-$I_2$) and control ($AlCl_3$) catalyst are summarized on Table IV.

TABLE IV

Preparation of Hexamethylindane (HMI) from p-Cymene and 2-Methylbutene-2 Using $AlCl_3$—$I_2$ as Catalyst

| Catalyst | Reaction Time, minutes | % Conversion of p-cymene | % Selectivity to HMI |
|---|---|---|---|
| $AlCl_3$—$I_2$ (Invention) | 20 (Addition Complete) | 74 | 87 |
|  | 80 | 75 | 88 |
| $AlCl_3$ (control) | 22 (Addition Complete) | 69 | 86 |
|  | 82 | 71 | 84 |

The results of this example demonstrate that invention catalyst provides both improved conversion of p-cymene and improved selectivity to hexamethylindane product compared to control catalyst.

EXAMPLE V

This example demonstrates the use of a mixture of two olefins in a cyclialkylation reaction in which there is a preferential conversion of one olefin, via reduction, to the alkane. As noted earlier, for each mole of olefin consumed in the cyclialkylation process, another mole of the olefin is reduced to the alkane.

To 129 grams (0.96 mole, 150 mL) of p-cymene was added 7 grams (0.052 mole) of aluminum chloride and 2 grams (0.008 mole) of iodine under nitrogen atmosphere. The mixture was stirred rapidly and a mixture of isobutylene and neohexene was added in the liquid phase beneath the surface of the p-cymene containing the catalyst. The rate of addition of the olefin mixture was regulated over a 15–30 minute period such that the reaction temperature was maintained in the range of 30°–35° C. The reaction was continued so that the total of addition time plus additional stirring time was 60 minutes. A sample was taken and analyzed by glc. The results of a series of runs in which the ratio of the moles of total olefin to p-cymene was kept constant while the ratio of the neohexene to isobutylene was varied is shown in Table V.

TABLE V

Utilization of Neohexene (NH) Cyclialkylation With $AlCl_3$—$I_2$ Catalyst in the Presence of Isobutylene (IB)

| Mole Ratio IB/NH | p-Cymene Conv., % | Mole Ratio* PMI/HMT | Change in Ratios | % Change in Ratio |
|---|---|---|---|---|
| 0 | 96.1 | 0 | 0 | — |
| 0.14 | 94.9 | 0.16 | +0.02 | +14 |
| 0.32 | 96.1 | 0.29 | −0.03 | −9 |
| 0.47 | 96.6 | 0.38 | −0.09 | −19 |
| 0.56 | 97.8 | 0.46 | −0.10 | −18 |
| 0.67 | 95.0 | 0.49 | −0.18 | −27 |
| 0.77 | 96.4 | 0.57 | −0.20 | −26 |
| 0.92 | 93.1 | 0.68 | −0.24 | −26 |
| 1.50 | 96.3 | 1.29 | −0.21 | −14 |
| 2.50 | 89.0 | 1.85 | −0.65 | −25 |

*PMI = 1,1,3,3,5-Pentamethylindane
HMT = 1,1,3,4,4,6-Hexamethyltetralin

The major product from the reaction of p-cymene with neohexene (NH) is 1,1,3,4,4,6-hexamethyl-1,2,3,4-tetrahydronaphthalene (HMT) while the reaction of p-cymene with isobutylene (IB) produces 1,1,3,5,5-pentamethylindane (PMI). Both are formed in the reaction when the mixture of olefins is added; however, the ratio of the isobutylene to neohexene in the reaction mixture is not the same as the ratio of corresponding products, i.e., PMI to HMT, in the product mixture. It is seen in Table V that when the isobutylene is about 50% or more of the olefin mixture, the proportion of isobutylene converted to cyclialkylation product is significantly lower than the proportion of isobutylene in the initial olefin reactant mixture. This means that there is preferential reduction of isobutylene to isobutane and a corresponding greater utilization of the more expensive olefin, neohexene, in the cyclialkylation reaction, rather than in the reduction of neohexene to the alkane, neohexane.

EXAMPLE VI

The procedure described in Example V was repeated, once with a catalyst consisting essentially of $AlCl_3$ only, once with a catalyst consisting essentially of $AlCl_3$-$I_2$ and once with a catalyst consisting essentially of $AlCl_3$-HI. In all runs, 150 mL (130 g, 1 mole) of p-cymene was employed. In the invention run, 7 g (0.05 mole) of $AlCl_3$ and 2 g (0.0008 mole) of iodine were employed. In the control run, 20 g (0.15 mole) of $AlCl_3$ was employed. In the comparison run, 7 g (0.05 mole) of $AlCl_3$ and 5 g (0.04 mole) of HI was employed. Samples were taken for analysis by glc when mixed olefin addition was complete and at various intervals thereafter. Results are summarized in Table VI.

TABLE VI

Alkylation of p-Cymene with Mixed Olefins

| Catalyst | Reaction time, Minute | p-Cymene conv. | Mole Ratio NH/IB | Mole Ratio HMT/PMI |
|---|---|---|---|---|
| $AlCl_3$—$I_2$ (invention) | 20 (olefin addition complete) | 90 | 1.2 | 1.5 |
|  | 30 | 92 | 1.2 | 1.5 |
|  | 60 | 93 | 1.2 | 1.5 |
| $AlCl_3$ (Control) | 120 (olefin addition complete) | 88 | 1.5 | 1.3 |
|  | 160 | 92 | 1.5 | 1.3 |
| $AlCl_3$—HI (Comparison) | 28 (olefin addition complete) | 96 | 1.3 | 1.0 |
|  | 38 | 98 | 1.3 | 1.0 |
|  | 88 | 99 | 1.3 | 1.0 |

The results of this example demonstrate that preferential consumption of the less expensive olefin, isobutylene, occurs only with the invention catalyst. Thus, the ratio of HMT (hexamethyltetralin; neohexene cyclialkylation product) to PMI (pentamethylindane; isobutylene cyclialkylation product) is significantly increased compared to the ratio of olefins in the feed when $AlCl_3$-$I_2$ catalyst is used. Conversely, the ratio of HMT/PMI is reduced compared to the ratio of olefin feed with control catalyst, i.e., $AlCl_3$ alone. Similarly, the ratio of HMT/PMI is reduced compared to the ratio of olefin feed with comparison catalyst, i.e., $AlCl_3$-HI. These results demonstrate that $I_2$ is not converted to HI under the reaction conditions employed, since HI does not provide a beneficial effect on the cyclialkylation reaction, as does $I_2$.

EXAMPLE VII

The procedure of Example III was repeated except meta-xylene (200 mL; 172 g; 1.6 mole) was employed as the aromatic component. A sample was taken immediately upon completion of addition of isobutylene to the reaction mixture and analyzed by glc. The isobutylene addition took about one hour. Results with AlCl$_3$ alone (10 g; 0.07 mole) and AlCl$_3$-I$_2$ (10 g-2.5 g; 0.07 mole-0.01 mole) at 2 different reaction temperatures are summarized in Table VII.

TABLE VII

Production of Tertiarybutyl meta-Xylene (TBMX) from meta-Xylene and Isobutylene

| Catalyst | % xylene conversion | % Sel. To TBMX |
|---|---|---|
| (a) Reaction at 55° C. | | |
| AlCl$_3$—I$_2$ (invention) | 79 | 75 |
| AlCl$_3$ (control) | 63 | 47 |
| (b) Reaction at 70° C. | | |
| AlCl$_3$—I$_2$ (invention) | 85 | 79 |
| AlCl$_3$ (control) | 68 | 59 |

Both xylene conversion and selectivity to the desired primary product, tertiarylbutyl meta-xylene, are increased with the invention catalyst, AlCl$_3$-I$_2$, compared to control catalyst, AlCl$_3$ only, at reaction temperatures of 55° and 70° C.

EXAMPLE VIII

The reaction of toluene with isobutylene was carried out with AlCl$_3$ alone and AlCl$_3$-I$_2$ as catalyst at both 30° C. and at 60° C. For reaction at 30° C., 150 mL (130 g; 1.4 mole) of toluene and 10 g (0.07 mole) of AlCl$_3$, optionally with 2 g (0.008 mole) of I$_2$, were mixed in a well-stirred reaction vessel while isobutylene was added over a 2-hour period, samples being taken every 20 minute for glc analysis. Results are summarized in Table VIII (a).

For reaction at 60° C., 100 mL (87 g; 0.9 mole) of toluene and 8 g (0.06 mole) of AlCl$_3$, optionally with 2 g (0.008 mole) of I$_2$, were mixed in a well-stirred vessel while isobutylene was added over a 4-hour period, samples being taken every 40 minute for glc analysis. Results are summarized in Table VIII (b).

TABLE VIII

Alkylation of Toluene with Isobutylene

| Catalyst | Reaction time, minute | % Conversion of Toluene | % Selectivity* m-TBT | p-TBT | di-TBT |
|---|---|---|---|---|---|
| (a) Reaction at 30° C. | | | | | |
| AlCl$_3$—I$_2$ (invention) | 20 | 24 | 53 | 26 | 1 |
| | 40 | 56 | 51 | 28 | 5 |
| | 60 | 78 | 46 | 26 | 12 |
| | 80 | 93 | 34 | 24 | 28 |
| | 100 | 98 | 18 | 23 | 45 |
| | 120 | 100 | 4 | 15 | 50 |
| AlCl$_3$ (control) | 20 | 28 | 42 | 21 | <1 |
| | 40 | 51 | 39 | 23 | 2 |
| | 60 | 66 | 40 | 23 | 5 |
| | 80 | 84 | 31 | 22 | 9 |
| | 100 | 84 | 31 | 22 | 9 |
| | 120 | 99 | 10 | 18 | 28 |
| (b) Reaction at 60° C. | | | | | |
| AlCl$_3$—I$_2$ (invention) | 40 | 34 | 56 | 28 | 3 |
| | 80 | 75 | 46 | 26 | 10 |
| | 120 | 97 | 24 | 20 | 36 |
| | 160 | 99 | 7 | 18 | 50 |
| | 240 | 99 | 3 | 16 | 52 |
| AlCl$_3$ (control) | 40 | 30 | 46 | 24 | <1 |
| | 80 | 66 | 32 | 21 | 3 |
| | 120 | 88 | 24 | 24 | 10 |
| | 160 | 98 | 11 | 26 | 23 |
| | 200 | 99 | 5 | 24 | 28 |
| | 240 | 99 | 4 | 25 | 29 |

*m-TBT = meta-tertiarybutyltoluene
p-TBT = para-tertiarybutyltoluene
di-TBT = di-tertiarybutyltoluene, i.e., 1-methyl-3,5-di-tertiarybutylbenzene The selectivity to the desired product, di-tertiarybutyltoluene, is significantly increased (nearly doubled) with the inventive catalyst (AlCl$_3$-I$_2$) compared to control catalyst (AlCl$_3$ alone). In addition, the rate of toluene conversion appears to be more rapid with invention compared to control catalyst.

EXAMPLE IX

Alkylation of Xylenes with Neohexene

Five grams of anhydrous aluminum chloride (0.04 mole) and 5 g (0.02 mole) of I$_2$ were added to 150 mL (130 g; 1.2 mole) of ortho- or meta-xylene. The reaction mixture was stirred rapidly and 120 mL (78 g; 0.9 mole) of neohexene added dropwise over about 7–10 minutes, while the pot temperature was maintained at about 30°–35° C. with external cooling. When neohexene addition was complete, a sample was taken for analysis by glc. The reaction mixture was then stirred an additional 10 minutes at room temperature, then sampled again for glc analysis. The analyses from the reaction of ortho-xylene and meta-xylene with neohexene in the presence and absence of added I$_2$ are summarized in Table IX.

TABLE IX

Alkylation of Xylene with Neohexene

| Catalyst | Reaction time, minutes | % Conversion of xylene | % Selectivity* TBX | TAX | SHX | THX |
|---|---|---|---|---|---|---|
| (a) ortho-xylene** | | | | | | |
| AlCl$_3$—I$_2$ (invention) | 7 (neohexene addition complete) | 71 | 5 | 3 | 23 | 62 |
| | 17 | 70 | 5 | 3 | 25 | 60 |
| AlCl$_3$ (control) | 9 (neohexene addition complete) | 72 | 2 | 2 | 22 | 68 |
| | 19 | 71 | 2 | 2 | 25 | 65 |
| (b) meta-xylene*** | | | | | | |
| AlCl$_3$—I$_2$ (invention) | 9 (neohexene addition complete) | 68 | 19 | 8 | 4 | 56 |
| | 19 | 68 | 20 | 9 | 7 | 51 |
| AlCl$_3$ | 10 (neohexene addition complete) | 73 | 7 | 3 | 3 | 79 |

TABLE IX-continued

| | Alkylation of Xylene with Neohexene | | | | | |
|---|---|---|---|---|---|---|
| | | % Conversion | % Selectivity* | | | |
| Catalyst | Reaction time, minutes | of xylene | TBX | TAX | SHX | THX |
| (control) | 20 | 73 | 8 | 3 | 6 | 77 |

*TBX = tertiarybutyl xylene
TAX = tertiaryamyl xylene
SHX = secondarylhexyl xylene
THX = tertiaryhexyl xylene
**Ortho-xylene products are 1,2,4-trisubstituted benzenes.
***meta-xylene products are 1,3,5-trisubstituted benzenes.

The reaction of ortho-xylene with neohexene appears to be relatively insensitive to the alkylation catalyst employed, since results with both $AlCl_3$-$I_2$ and $AlCl_3$ catalysts are comparable. Similarly, reaction of meta-xylene with neohexene appears to be relatively insensitive to the alkylation catalyst employed. In both cases, xylene conversions are comparable with either catalyst.

I claim:

1. A process comprising contacting
    (a) at least one monocyclic, bicyclic or tricyclic aromatic compound having 6 up to 30 carbon atoms and
    (b) at least one olefinic compound having the formula

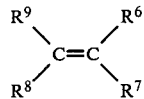

wherein each of $R^6$ through $R^9$ is independently selected from hydrogen and $C_1$ through $C_{10}$ alkyl or cycloalkyl radical; or $R^6$ and $R^7$ or $R^6$ and $R^9$ can be joined as part of a polymethylene or alkyl- or cycloalkyl-substituted polymethylene radical having two to about 20 carbon atoms, wherein said olefinic compound has 4 up to 30 carbon atoms, and wherein said olefinic compound is capable of forming a tertiary carbocation under the process conditions in the presence of a catalyst consisting essentially of
    (i) $AlX_3$ and
    (ii) $I_2$;
wherein each X is individually selected from the halogens.

2. A process in accordance with claim 1 wherein said (a) aromatic compound has the formula

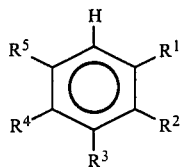

wherein each of $R^1$ through $R^5$ is independently selected from hydrogen and $C_1$ through $C_{10}$ alkyl or cycloalkyl radical.

3. A process in accordance with claim 2 wherein $R^1$ is methyl or ethyl and $R^4$ is a secondary alkyl or cycloalkyl radical having 3 to about 10 carbon atoms and only one alpha-hydrogen.

4. A process in accordance with claim 1 wherein the weight ratio of (ii):(i) is about 0.01 to about 1:1.

5. A process in accordance with claim 1 wherein the molar ratio of (i):(a) is about 0.01 to about 0.5:1.

6. A process in accordance with claim 1 wherein said at least one olefinic compound comprises a mixture of a first olefinic compound and a second olefinic compound wherein said first olefinic compound is a better hydrogen acceptor under the process conditions than said second olefinic compound.

7. A process in accordance with claim 6 wherein said first olefinic compound is isobutylene and said second olefinic compound is neohexene.

8. A process in accordance with claim 1 wherein said olefinic compound is isobutylene.

9. A process in accordance with claim 8 wherein said aromatic compound is toluene.

10. A process in accordance with claim 8 wherein said aromatic compound is meta-xylene.

11. A process in accordance with claim 1 wherein said olefinic compound is 2-methyl-2-butene.

12. A process in accordance with claim 1 wherein said olefinic compound is 2,3-dimethyl-1-butene.

13. A process in accordance with claim 1 wherein said olefinic compound is neohexene.

14. A process in accordance with claim 1 wherein said olefinic compound is 2-methyl-2-butene.

15. A process in accordance with claim 1 wherein said olefinic compound is 2,4,4-trimethyl-2-pentene.

16. A process in accordance with claim 1 wherein said aromatic compound is toluene.

17. A process in accordance with claim 1 wherein said aromatic compound is meta-xylene.

18. A process in accordance with claim 3 wherein said aromatic compound is p-cymene.

19. A process in accordance with claim 1 wherein said contacting is carried out in the presence of a diluent.

20. A process in accordance with claim 19 wherein said diluent is selected from the group consisting of said at least one monocyclic, bicyclic or tricyclic aromatic compound and the alkylated aromatic product which results from said contacting.

21. A process in accordance with claim 19 wherein said catalyst is added to said diluent to produce a slurry prior to adding said aromatic compound and said olefinic compound to said slurry.

22. A process comprising
    (1) combining a mixture consisting essentially of
        (i) $AlX_3$ and
        (ii) $I_2$;
        wherein each X is individually selected from the halogens, in an aromatic medium to produce a slurry,
    (2) adding to said slurry
        (a) at least one monocyclic, bicyclic or tricyclic reactant aromatic compound having 6 up to 30 carbon atoms and (b) at least one olefinic compound having the formula

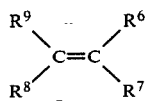

wherein each of $R^6$ through $R^9$ is independently selected from hydrogen and $C_1$ through $C_{10}$ alkyl or cycloalkyl radical; or $R^6$ and $R^7$ or $R^6$ and $R^9$ can be joined as part of a polymethylene or alkyl- or cycloalkyl-substituted polymethylene radical having two to about 20 carbon atoms, wherein said olefinic compound has 4 up to 30 carbon atoms, and wherein said olefinic compound is capable of forming a tertiary carbocation under the process conditions suitable for the formatio of alkylated aromatic product,
wherein said aromatic medium is selected from the group consisting of said at least one reactant aromatic compound, and said alkylated aromatic product, and mixtures thereof.

23. A method in accordance with claim 22 wherein said
(a) aromatic compound has the formula

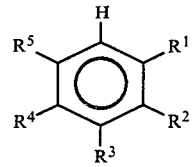

wherein each of $R^1$ through $R^5$ is independently selected from hydrogen and $C_1$ through $C_{10}$ alkyl or cycloalkyl radical.

24. A process in accordance with claim 22 wherein said reactant aromatic compound is p-cymene.

25. A process in accordance with claim 22 wherein said olefinic compound is isobutylene.

* * * * *